US011191227B2

(12) United States Patent
Ebert et al.

(10) Patent No.: US 11,191,227 B2
(45) Date of Patent: Dec. 7, 2021

(54) MOISTURE MANAGEMENT AND PERENNIAL CROP SUSTAINABILITY DECISION SYSTEM

(71) Applicant: Purdue Research Foundation, West Lafayette, IN (US)

(72) Inventors: David Scott Ebert, West Lafayette, IN (US); Christian E. Butzke, West Lafayette, IN (US); Susan Ebert, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 502 days.

(21) Appl. No.: 15/523,619

(22) PCT Filed: Nov. 2, 2015

(86) PCT No.: PCT/US2015/058683
§ 371 (c)(1),
(2) Date: May 1, 2017

(87) PCT Pub. No.: WO2016/070195
PCT Pub. Date: May 6, 2016

(65) Prior Publication Data
US 2017/0311559 A1 Nov. 2, 2017

Related U.S. Application Data

(60) Provisional application No. 62/073,731, filed on Oct. 31, 2014.

(51) Int. Cl.
*A01G 17/02* (2006.01)
*G01N 33/24* (2006.01)
(Continued)

(52) U.S. Cl.
CPC ............. *A01G 25/16* (2013.01); *A01G 17/02* (2013.01); *G01N 33/246* (2013.01);
(Continued)

(58) Field of Classification Search
None
See application file for complete search history.

(56) References Cited

U.S. PATENT DOCUMENTS 8,340,910 B1* 12/2012 Magro ...................... A01G 7/00
702/2
2004/0145379 A1* 7/2004 Buss ..................... G01N 33/246
324/664
(Continued)

FOREIGN PATENT DOCUMENTS

| WO | 2010129168 A2 | 11/2010 |
| WO | 2013012826 A1 | 1/2013 |
| WO | 2014073985 A1 | 5/2014 |

OTHER PUBLICATIONS

Zhu et al., "SoLIM: A New Technology For Soil Mapping Using GIS, Expert Knowledge & Fuzzy Logic", Jan. 1, 2007, University of Wisconsin-Madison (Year: 2007).*
(Continued)

*Primary Examiner* — Brent A. Fairbanks
(74) *Attorney, Agent, or Firm* — Reichel Stohry Dean LLP; Natalie J. Dean; Mark C. Reichel

(57) ABSTRACT

Disclosed herein are a system and method that integrate vineyard sensor data into an environment that enables analysis, historical trend analytics, spatio-temporal analytics, and weather model fusion for improved decision making from vineyard management to wine production. The integration of new sensor data from multiple soil depths with surface measurements, combined with production flow process and historical information enables new decision making capabilities. A wireless network of sensor/transmitters can be (Continued)

distributed to provide a 3-dimensional assessment of water movement both across the grower's field and as it moves from the surface through the root zone. The soil monitoring data stream feeds into a visualization interface that will be incorporated in software based decision aid and crop management tool that helps agricultural producers reduce costs, minimize water and nutrient applications, and better protect the environment by reducing agricultural production inputs.

20 Claims, 3 Drawing Sheets

(51) Int. Cl.
  E02D 1/04     (2006.01)
  A01G 25/16    (2006.01)
  G05D 7/06     (2006.01)
  G05D 22/02    (2006.01)
(52) U.S. Cl.
  CPC .......... *G05D 7/0629* (2013.01); *G05D 22/02* (2013.01); *E02D 1/04* (2013.01); *G05D 7/0617* (2013.01); *Y02A 40/22* (2018.01)

(56) References Cited

U.S. PATENT DOCUMENTS

| | | | |
|---|---|---|---|
| 2008/0184827 A1* | 8/2008 | Susfalk | G01D 9/005 73/866.5 |
| 2009/0150000 A1* | 6/2009 | Stelford | A01G 25/092 700/284 |
| 2009/0177330 A1 | 7/2009 | Kah, Jr. | |
| 2011/0035059 A1 | 2/2011 | Ersavas | |
| 2011/0238229 A1 | 9/2011 | Woytowitz et al. | |
| 2012/0284264 A1 | 11/2012 | Lankford | |
| 2012/0290140 A1* | 11/2012 | Groeneveld | A01G 25/16 700/284 |
| 2014/0236868 A1 | 8/2014 | Cook | |
| 2015/0040473 A1* | 2/2015 | Lankford | A01G 25/16 47/58.1 SC |

OTHER PUBLICATIONS

Smith et al., "Machine Learning Approaches for Soil Classification in a Multi-agent Deficit Irrigation Control System", Feb. 10-13, 2009, 2009 IEEE International Conference on Industrial Technology (Year: 2009).*
MacMilan et al., "Automated analysis and classification of landforms using high-resolution digital elevation data: applications and issues", 2003, Canadian Journal of Remote Sensing, vol. 29, No. 5, pp. 592-606 (Year: 2003).*
International Searching Authority, International Search Report, PCT Application Serial No. PCT/US2015/058683, dated Jan. 22, 2016.
Euopean Patent Office, European Search Report and Search Opinion, European Application Serial No. EP15856005, dated May 15, 2018.

* cited by examiner

MOISTURE MANAGEMENT AND PERENNIAL CROP SUSTAINABILITY DECISION SYSTEM

CROSS-REFERENCE TO RELATED APPLICATIONS

The present patent application is a 35 U.S.C. § 371 national phase application of PCT/US15/58683, filed Nov. 2, 2015, which is related to and claims the priority benefit of U.S. Provisional Patent Application Ser. No. 62/073,731, filed Oct. 31, 2014, the contents of which is hereby incorporated by reference in its entirety into this disclosure.

TECHNICAL FIELD

The present disclosure generally relates to data management, and in particular to a system and method to improve the ability of wine grape producers to manage their crops and water resources especially under drought conditions in order to: maximize income, increase yields and grape quality, improve long-term vine sustainability, minimize inputs and costs, conserve land and water resources and enhance the environment.

BACKGROUND

This section introduces aspects that may help facilitate a better understanding of the disclosure. Accordingly, these statements are to be read in this light and are not to be understood as admissions about what is or is not prior art.

Changing climatic conditions and current droughts are challenging agricultural producers to make the best possible use of scarce moisture resources and increasingly expensive irrigation water. These complex challenges are multifaceted, ranging from day-to-day and decisions throughout the entire growing season, to long-term multi-year crop sustainability issues. Moreover, these challenges are critical for both dry-farmed and irrigated fields. The challenge of managing the timing and amount of water is especially important in the grape and wine industries, where the timing and extent of moisture stress are important determinants of the quality, quantity, and value of the final product. Subsequently, wine quality and implied market value are mainly determined by the composition of the grape crop at harvest, and to a much lesser degree by the winemaking process itself, the equipment used, or the skill of the winemaker. There is also growing concern of crop maximization strategies on the fruitful lifetime of the vines and the large economic consequences of more frequent vineyard replanting. There is therefore an unmet need for technology for improved, high resolution and precision sensor data and tools that will enable making better decisions about water management choices using, as a minimum, data that is currently available.

In addition, while analytics companies are beginning to investigate these issues through "big data analytics" approaches, current tools do not sufficiently integrate physical models, translate raw data, nor correlate it with "real world" decisions. Easy to use, reliable software to turn sensor data, climatic data, soil data, plant physiology models, viticulture, enological models, and weather forecasts into easily understood and actionable, high-resolution, information crop management and irrigation decisions by the producer is therefore critically needed.

SUMMARY

According to one aspect, a method is provided, comprising using a computer, receiving temperature and moisture data from a plurality of temperature and moisture sensors, the sensors disposed within an agricultural field, determining a volumetric water content for an area of soil contained in the field, determining a level of spatial and temporal variability within the area, including variability through a root zone of the soil, determining a plant available water level for the area of soil, and displaying results of said evaluating on an electronic interface to a user. The method may also comprise determining a soil texture and composition profile for the area of soil. The method may also comprise determining a sensor calibration curve based on the soil texture and composition profile. The method may comprise calibrating the volumetric water content for the area of soil based on the sensor curve. The method may also comprise determining a soil pressure release curve based on the soil texture and composition profile for the area of soil. The method may also comprise adjusting the plant available water determination based on the soil pressure release curve. The sensor calibration curve may be determined from data received from the temperature and moisture sensors. The sensor calibration curve may also be determined from ALIM data. The method may also comprise, for each of a plurality of soil areas, determining a weighted interpolation of plant available water in the soil area from plant available water levels determined for a plurality of points within the soil area. The method may also comprise averaging determined values for plant available water, and generating a spatial map based on distance interpolation and topography to generating a flow simulation on an electronic display. The method may also comprise controlling an irrigation system operatively connected to the processor to adjust irrigation output based on the determined plant available water. The method may also comprise determining a predicted harvest date based on the received information. The method may also comprise updating the predicted harvest date based on newly acquired sensor data. The method may comprise predicting a composition variation of plant attributes. The method may also comprise said predicting is determined for separate blocks of the field. The method may also comprise creating a spatial variation map indicating plant component areas that are on a target, above target, or below target.

According to another aspect, a system is provided, comprising a memory, a computer processor operatively connected to the memory, a plurality of temperature and moisture sensors disposed within an agricultural field and operatively connected to the processor, wherein the processor is configured to receive temperature and moisture data from the plurality of temperature and moisture sensors, the sensors disposed within an agricultural field, determine a volumetric water content for an area of soil contained in the field, determine a level of spatial and temporal variability within the area, including variability through a root zone of the soil, determine a plant available water level for the area of soil, and display results of said evaluating on an electronic interface to a user. The processor may also be configured to determine a soil texture and composition profile for the area of soil. The processor may also be configured to determine a sensor calibration curve based on the soil texture and composition profile. The processor may also be configured to calibrate the volumetric water content for the area of soil based on the sensor curve. The processor may also be configured to determine a soil pressure release curve based on the soil texture and composition profile for the area of soil. The processor may also be configured to adjust the plant available water determination based on the soil pressure release curve. The sensor calibration curve may also be determined from data received from the temperature and moisture sensors. The sensor calibration curve may also be determined from ALIM data. The processor may also be configured to for each of a plurality of soil areas, determine a weighted interpolation of plant available water in the soil area from plant available water levels determined for a plurality of points within the soil area. The processor may also be configured to average determined values for plant available water and generate a spatial map based on distance interpolation and topography to generating a flow simulation on an electronic display. The processor may also be configured to control an irrigation system operatively connected to the processor to adjust irrigation output based on the determined plant available water. The processor may also be configured to determine a predicted harvest date based on the received information. The processor may also be configured to update the predicted harvest date based on newly acquired sensor data. The processor may also be configured to predict a composition variation of plant attributes. The processor may also be configured to determine said predicting for separate blocks of the field. The processor may also be configured to create a spatial variation map indicating plant component areas that are on a target, above target, or below target.

DETAILED DESCRIPTION

Figure 1:
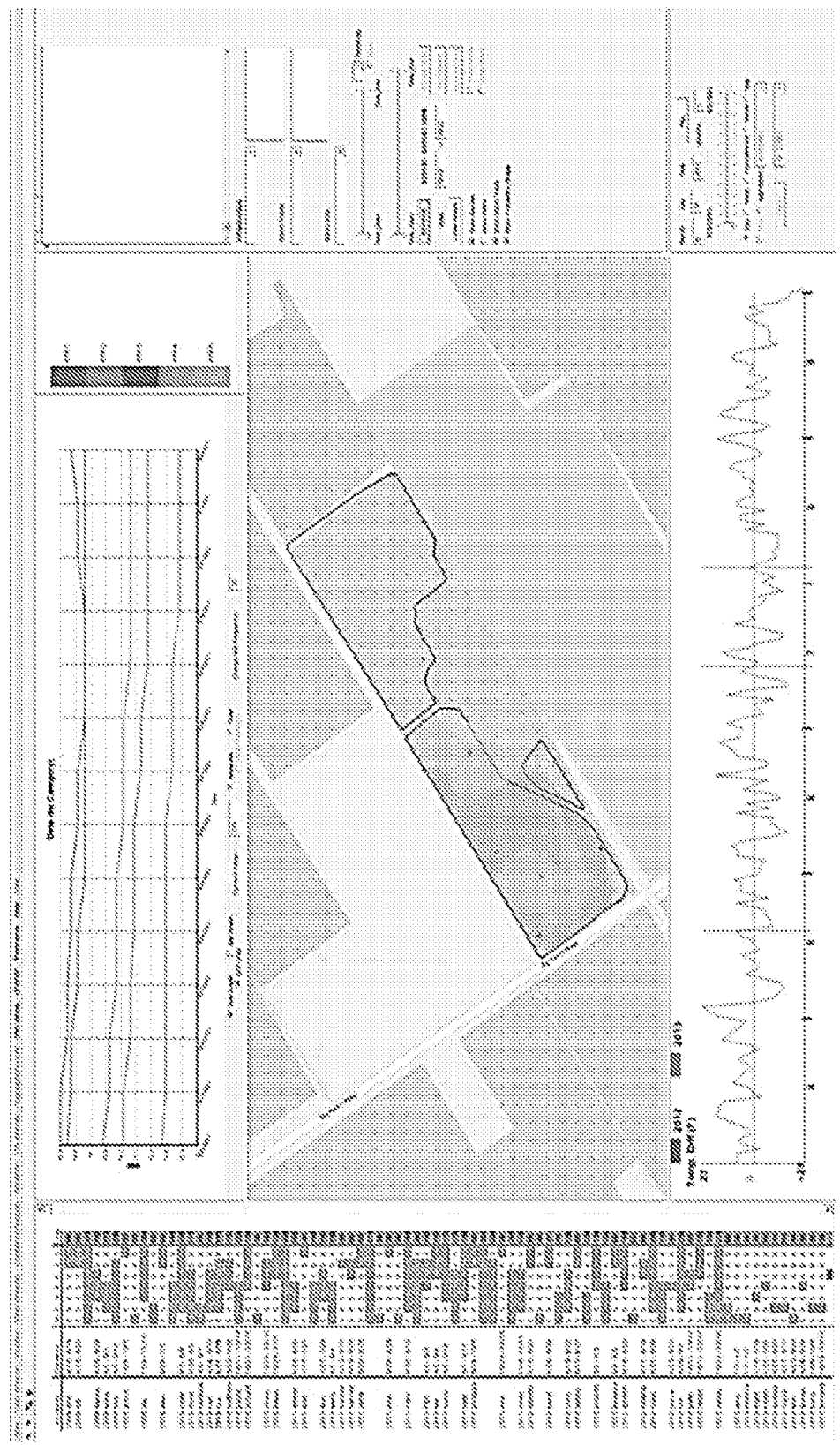
FIG. 1 shows a screenshot of a user interface showing a soil data according to one embodiment.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Disclosed herein is an effective decision support software system 1000 (FIG. 3) based on sensing technology (in situ and remotely sensed) to enable producers, field managers, and winemakers to manage soil moisture, pruning, irrigation, canopy management, and water conservation to increase production efficiency, quality, and crop and sustainability, while reducing variability in production within a field and across seasons. This sensor network combines in-field moisture and temperature sensors to track the availability and characteristics of soil moisture and temperature at a high level of data resolution throughout the crop root zone and soil profile. The network makes it possible to provide a 3-dimensional assessment of water movement through the soil and across the grower's field making it possible to respond to spatial and temporal variations in the vineyard in real time. This information will greatly help producers plan and minimize the costs of cover crop decisions, irrigation, and other management practices. The soil monitoring data stream is combined and compared with plant-based sensors and referenced against coarser current sensor technologies. The resulting large volume of environmental sensor data are analyzed, enhanced with physical models, and transformed using visual analytics into a useful interactive software decision making environment using easily understood visual metrics and graphics.

In addition, while for demonstrative purposes the focus of this disclosure is on vineyards, the agricultural management tools disclosed herein may be used with and are of immediate importance to many other high value horticulture crops (including fruit, nut, and tree producers) and are a beneficial resource for many more agricultural crops as well.

Relation of Soil Moisture and Temperature to Wine Grape Production:

Throughout the world, grapevines grow in all kinds of soil. The factors controlling soil formation are universally present, but their individual influence and subtle interactions vary greatly from place to place, giving rise to soil variability and management challenge. Success in the production of an optimum yield of quality grapes, with minimum impact on the environment, will depend on how well vineyard managers understand high-resolution soil variability, its impact on vine and grape stress and nutrient flow, and how well they are able to work with this variability, or are able to modify it to their own ends. Outside the well-established wine regions, the practical assessment of a new site's terroir is hampered by the fact that the causal relationships and interactions between particular soil properties and local moisture and temperature conditions are not known. Moreover, even in well-established vineyards, these causal relationships are not based on thorough, validated scientific models of the processes and causal relationships between surface through root-zone temperature, moisture, soil composition, and desired harvest characteristics.

Evaluations and modeling of the vast range of winegrowing and winemaking parameters by artificial neural networks have consistently shown that basic vineyard parameters such as air and soil temperature and moisture profiles throughout the current and previous growing seasons have the most important impact on grape composition.

Moreover, the ability of the winemaker to base processing decisions on predictable grape composition is crucial in order to make the highest quality wines in any given vintage. Knowledge of and control over irrigation needs and application in the vineyard enable the winemaker to access and manipulate flavor development and ripeness, nutrient pickup, as well as grape berry size and polyphenol composition. Depending on the vineyard soil composition, including drainage structure, water holding capacity, pH buffering capabilities, latent heat absorption and surface sunlight reflection, the regulation, onset, and physical uptake of nutrients into the scion sap and ultimately the berries, is greatly influenced by the resulting temperature and water status of the root system. Depending on the application, these parameters are not easily accessed and do not necessarily correspond to traditional above-ground measurements. The uptake of nutrients from the soil, particularly potassium, calcium, nitrogen, iron, and sulfur, have a most pertinent impact on wine aroma development during and after fermentation. Winery post-harvest decisions related to skin contact time, yeast nutrition supplementation, color and tannin extraction techniques, and other choices to further elevate and stabilize the wines, are best made with the most complete knowledge about the composition of the incoming fruit.

Soil monitoring is a useful tool for developing an understanding of the interplay between soil and environmental conditions, and specifically to learn how to optimize water allocations, cover crop decisions, tillage decisions, and irrigation scheduling but only if it: (1) is measured at multiple depths and at least as deep as the bottom of the root zone; (2) is measured continuously, not in weekly snapshots; (3) is installed to capture as nearly as possible the center of the wetted "bulb" of soil; and (4) is placed in an area of the vineyard where soil has some of the lowest water holding capacity. The minimum number of measurement depths is 2, but ideally measurement depths of at least 1-foot intervals are monitored. The purpose of this is to gauge how deeply the rain water and irrigation applications are infiltrating. The goal is, in general, wet to the bottom of the root zone and no deeper. Measuring soil moisture at several depths, and identifying patterns of wetting following irrigation, gives useful feedback and allows growers to "calibrate" their irrigation volumes to match the desired depth of wetting.

Not enough or too much soil moisture can be damaging to the plant and crop yields, depending on the severity and timing of the shortage or excess. When vines are well watered, they have actively growing shoot tips and normal internode expansion. However, if water is too readily available, especially during the period of rapid shoot growth from preflowering to veraison, excess vigor may result that can cause excessive fruit shading. Water stress at flowering can reduce fruit set. From fruit set to veraison, moderate to severe stress reduces berry size. During ripening, mild water stress enhances the accumulation of soluble solids in the berries by suppressing vegetative growth, but more severe stress decreases berry size. In this case, sugar accumulation and flavor development are delayed as a result of decreased photosynthesis and premature leaf fall. During the final ripening period, however, a gradual increase in stress enhances the intensity of flavors in the berries, so that outstanding vintages are produced in years of dry and hot mid to late summers in Europe's classic wine growing regions. This natural response to a changing water supply seldom occurs in hot inland regions where irrigation is essential to grow grapes. Instead, growers rely on manipulating the amount and timing of irrigation to control vigor and enhance grape quality.

An ideal moisture monitoring system, therefore, needs to be able to assess soil moisture at depth and across the field to understand spatial variability, as well as calibrate the moisture data against the soil type and crop being grown in order to provide useful information to growers and managers about actual water availability to the crop. The timing of moisture is particularly important to grapes and grapevines, as a certain amount of moisture stress is desired at the right time in the development of the grape clusters, in order to acquire the complex mix of sugars and in order to develop the unique and ideal characteristics of the varietal being produced. Ideally, a steady stream of real time moisture data can be combined with high-resolution vineyard weather data, as well as GIS mapping of a vineyard that identifies the unique mix of soil conditions and characteristics across the vineyard to allow grapevine managers with the tools to manage by section of the vineyard, by rows, and even by individual plants.

Environmental Sensor and Soil Monitoring:

Remote sensing imaging technologies, which provide continuous spatial coverage over extended areas, are complementary to in situ sensing, that provides time series of information at specific locations. Spectral sensing can also provide information on the impact of soil moisture conditions on vegetation, and is critical for irrigation.

Remote sensing based soil moisture products provide information on the top 2-4 cm of the soil, and are primarily derived from microwave remote sensing data acquired by satellites. However, for vineyards, fruit and nut production, this is only a small fraction of the root zone and is insufficient for water management for these crops. Currently available data products from passive microwave sensors have extremely coarse spatial resolution (e.g., data products at ~50 km). The upcoming NASA SMAP mission, will combine inputs from active and passive microwave sensors to provide a blended product at 9 km, providing significant improvements to operational crop productivity and water stress estimates, as well as inputs to agricultural prediction models. However, while constraining model based estimates of soil moisture in the profile, these data products only provide boundary conditions. Augmenting SMAP with in situ sensing should provide dramatic improvements to 3D characterization of local soil moisture. Over extended areas, in situ point based estimates are also invaluable in both calibration/validation of the satellite based products and for downscaling these products to higher spatial resolutions.

Additionally, vegetation water content is an important indicator of plant health during the growing season, as well as being a contributor to remote sensing based estimates of soil moisture derived from passive microwave sensors. Plant stress directly or indirectly related to water shortage is also visible in the thermal infrared portion of the spectrum. The long established crop water stress index (CWSI) is based on water stress inducing stomatal closure, resulting in decreased evaporative cooling and increasing leaf temperature. Many remote sensing techniques for monitoring plant stress have been investigated.

In situ sensors provide quantitative results and can be more time- and cost-effective than conventional laboratory analyses and significantly higher-resolution than remote sensing dat). They are becoming smaller, faster, more accurate, more energy efficient, wireless, and more intelligent. Many such devices can be used for in situ (proximal) soil sensing—for example, ion-sensitive field effect transistors (ISFETs) used to measure soil pH and soil nutrients, or portable visible—near-infrared (vies—NIR) spectrometers to measure soil properties like organic carbon content and mineral composition. Worldwide, a considerable amount of research is being conducted to develop these soil sensors and techniques for their use in various applications. Many of these sensors are currently in a developmental phase and are used primarily in research, while others are available commercially. The most common techniques relate to the use of EMI and soil vies—NIR spectroscopy.

The full range of available soil moisture and crop monitors, as well as developing technology can be integrated into the crop management system 1000 of the present disclosure. However, the real challenge is not providing this massive data to the growers and producers, but determining what data sources are relevant, integrating soil models, plant physiology, and viticulture and enological research models to process, correlate, extract, interpret, and present succinct, reliable, relevant information for decision making.

Wireless Sensor Networks:

Wireless sensor networks can be used for continuous and realtime monitoring of soil properties such as soil water and nutrients for irrigation. Commercial systems for monitoring soil water using wireless telemetry are currently available; for example, capacitance probes linked to mobile telephone systems or radio networks are being used in irrigated agriculture. Irrigation systems managers can then use the data collected to optimize the use of resources in response to dynamic changes in soil condition and reduce the risk of water stress in crops. The main problems with currently available wireless sensing are durability, large sensor drift, difficulties with in situ calibration, and most importantly, inability for deep soil sensing throughout the root zone. To date, these systems are essentially above ground or within a few inches of the soil surface. Using prior art systems, it has not been possible to develop large networks that monitor environmental conditions within the soil through the root zone. According to one aspect of the present disclosure, low-frequency wireless moisture sensors will be implemented throughout the root-zone of common grape vine root stocks (0-3+ meters). The sensed data is received by the system 1000 of the present disclosure to provide and improve the data and cost-effectiveness of high-density deployment of sensors for crop management.

Sensor Networks: Underground Wireless Low-Frequency Transmitter/Sensor Systems:

As mentioned above, technology for deep soil wireless sensor networks can employ current commercial sensor packages for moisture, temperature, electrical conductivity, and possible some basic soil chemistry, as well as integrated new sensor technology as they become available.

Current research efforts to aid growers improve water management and crop management can be grouped into three categories: development of novel in-ground sensing technology; improvement in remote sensing for agriculture; and big data analytics for agriculture (smart agriculture). Traditional in-ground sensing has required wired sensing, although over the last several years some research has been conducted to develop underground sensor networks, but these efforts have been greatly limited by the attenuation of their transmitter signals by the soil itself. Despite the widely recognized importance of moisture monitoring, in a wine industry survey in 2013, a full 71% of growers said that they use no soil moisture device at all. This is because prior art devices do not produce a clean and repeatable signal by which to quantify moisture patterns in a way that enables them to make management decisions. Prior art systems only measure at the surface or take shallow readings, or provide coarse temporal reading, and are often cumbersome for practical use: they do not provide useful management information about moisture availability and movement across the vineyard as well as at moisture movement through the root zone. As described above, there have also been improvements in applying remote sensing to agriculture.

In turning this sensed data into management information, data analytics companies have also entered the smart agriculture arena and have started applying big data analytics (e.g., IBM) and machine learning to find correlations and develop statistics based predictive models for agricultural crops. Unfortunately, these efforts tend to simplify and over automate the proposed solutions. Most of these efforts work at too coarse a scale to solve the very high within vineyard variation, accurately account and integrate multiple sensor modalities that are properly registered and calibrated to enable effective decision making, and most importantly, fail to integrate physically-based research and models of the soil, environment, and plant.

According to one aspect of the present disclosure, a crop management system 1000 is provided which combines in situ and remotely sensed moisture and temperature data with physical models of the soil, environment, vine, and the winemaking process into an interface format that can aid growers and producers in improving their crop management practices, water management practices, and vineyard sustainability. The present disclosure focuses on developing these models, determining the necessity and practicality of various sensed data, and how these can be integrated into the decision making processes throughout the growing cycle and for long-term decision making. The presently disclosed system 1000 turns this data deluge into understandable, relevant information for crucial management decision points throughout the year through an intuitive visualization, analysis, and decision making platform.

Methodology:

In one test example, a suite of commercial soil sensors and weather stations is utilized to collect baseline data in the two commercial vineyards in Napa, Calif. The commercial soil sensors are connected to dataloggers to measure soil moisture, water potential, and temperature at four to five depths (1 ft. through 9 ft.) of the vine root zone at 3 to 7 locations in each vineyard that have varying soil types and topography. With the different soil types, a range of physiological and water stress responses will be elicited by the vines at the same water and irrigation level; this provides a rich dataset for visual analytics and irrigation model parameterization and validation.

Using data from the test example, the following considerations are explored:

1) What vertical spacing of sensors is needed throughout the root zone?

2) How does soil composition variation affect variation of sensor reading across the vineyard?

3) Does grape varietal or clone affect variation of sensor reading across the vineyard?

As part of the test example, at regular intervals of the growing season, plant growth (shoot length) was monitored for estimation of crop coefficients (for ET calculation) as well as to correlate with soil moisture utilization (based on estimates of exposed leaf area).

Moreover, the continuous micrometeorological, as well as soil moisture and temperature data, were used to generate visual maps of the spatial and temporal evolution of soil moisture in relation to canopy size, vine stress, and environmental variables to support irrigation, tillage, and nutrient decision support systems that can be used by growers.

The presently disclosed system 1000 also correlates and evaluates the incorporation of remotely sensed data with the in situ sensed data to determine (1) the value of integrating the two types of data, (2) the potential for fewer permanent in situ sensors if remotely sensed data is practically available to be integrated and calibrated with the in situ sensors and incorporated into our vineyard and vine models, and (3) the comparative and complimentary benefit of each modality for vineyard and production decision making.

At harvest, grapes are sampled near each sensor location and have complete lab analysis performed on phenolics, as well as basic chemical analysis to enable analytical and physiological relationships to measured data, as well as correlation to initial and evolving research model predictions. Additionally, grapes are sampled at each site at veraison to analyze, improve, and validate our viticulture and enological models of environmental effects (e.g., moisture, surface and root zone temperatures) from bud break to veraison on grape composition/quality (e.g., nutrient uptake, acid, Brix, and phenolics) and volume/yield.

Visual Analytics: Effective Decision Making Environments:

As previously mentioned, turning the massive data from vineyard sensors into useful information for effective decision making and management in wine grape growing, harvesting, and wine production is a true "big data" problem that needs aggregation, analytics, visualization, and interface development to turn this data into useful, actionable information for the vineyard manager and winemaker. Unfortunately, prior art big data analytics solutions fail to solve this type of problem where the data does not contain all the information for decision making (incomplete context), where the data is vague/fuzzy, and where it contains unquantified dependencies that occur in this situation with many interwoven physical processes (Brooks 2013). This is exactly where the integrated, interactive decision making environment of the presently disclosed system 1000 with the user driving the analysis and decision making is vital. Visual analytics, the science of analytical reasoning facilitated by interactive visual interfaces, provide the appropriate framework and approach for this decision making environment with big sensor data. Therefore, the disclosed system 1000 considers the grower and producer end-users, as well as domain experts from multiple domains into the development process to ensure an efficient and effective solution. The disclosed system further provides spatiotemporal analysis techniques and develops evolving predictive models of the incoming temporal, spatial, and spatiotemporal data, as well as creates proactive and predictive visual analytics environments that can be easily and effectively used by casual experts.

The presently disclosed system 1000 also addresses common grower questions, such as the following:

How does this season compare to 2010 and 2012?

Which growing season do the current conditions most closely match and what are the significant differences?

What is the vine stress level across each row and block?

How effective will irrigation this week be in terms of vine stress level and nutrient up-take?

What time of day and which day this week should I irrigate each section of each block for most effective management?

The presently disclosed system 1000 provides an integrated visualization and analysis environment that puts the vineyard manager, grower, and winemaker in control of the decision making, and partners their knowledge with data driven vine and vineyard models, as well as automated data analysis techniques. This environment enables them to harness information about what is happening in the vineyard to make effective crop management decisions, while also having information available that can be used in wine making to record, analyze, and understand characteristics of the growing conditions that can affect primary fermentation, secondary fermentation, phenolic production and characteristics, and aging decisions. The system 1000 makes them effective in their job without requiring them to become experts in using analytical software—thereby empowering them to do their job effectively without having to gain specific analytical skills.

Besides the in situ and remotely sensed data, the disclosed system 1000 also incorporates high resolution local climatology data, weather forecast data available from NOAA and other sources, models of nutrient uptake processes, hydrological models tailored to our specific vineyard conditions, and grower experience and insight data into the decision making process for water management (e.g., when to water, duration and type of irrigation plan, viability of varying deficit irrigation strategies), when to treat certain blocks with certain chemicals, cover crop composition and tillage decisions (e.g., no cover crop, tilled cover crop, mowed cover crop) and how to better understand vine stress during the entire growing season, as well as the long-term vine vitality and viability. The presently disclosed system 1000 further incorporates novel temporal data analysis, anomaly detection, and predictive modeling capabilities to analyze, model, and visualize the spatial and temporal data. The system 1000 further provides effective representations that enable correlation and comprehension of this streaming, multimodality, and multisource data and develop the appropriate visual representation for planning and decision making based on the end user's model of the sensed environment and system 1000. The system 1000 further determines the natural aggregation level for correlation analysis of the different soil and weather conditions for improved decision making.

The system and method disclosed herein may also comprise an effective daily dashboard for the growing season for each targeted user group (e.g., vineyard and irrigation manager, grower, winemaker) that allows the comparison of current soil and weather conditions across the vineyard to previous growing season information, including weather forecasts, growth cycle information and models for final harvest grape composition estimates (acid, pH, sugar, phenolics) so that growers and vintners can make effective management decisions. An example interface is shown in FIG. 1 (FIG. 1 is a screenshot image showing a visual analytic environment with soil moisture plotted (top), spatial moisture distribution (middle), temperature (bottom), and a data calendar view). The system 1000 further provides novel capabilities to compare the current soil condition variations across a vineyard to production data from previous years for each block or even row (e.g., harvest weight of each block vs. production weight after sorting, pH, TA, Brix, phenolic, and full acid profile at harvest). By incorporating enological and viticultural models of soil conditions and current plant status, the system 1000 translates this low level data into vine and fruit conditions that is more natural and intuitive to the growers and winemakers that enable them to collectively make decisions. Moreover, this interactive historical, current, and predictive spatial and temporal visualization environment provides new information and potentially new insights from visual analysis that can be confirmed or correlated by the built-in analytics and models. Our visual dashboard system is effective not only for daily management but also built to enable seasonal and harvest management, crop prediction, sustainability (e.g., vine fruitful years) and business economic impacts and models.

The disclosed system 1000 uses high spatial and temporal resolution soil and micrometeorological data from the received field data to develop a model to inform water management practices, helping growers with precision management at a finer spatial scale than available previously, potentially resulting in significant water savings. Additionally, variations in soil type and depth are accounted for based on dynamic information from the soil sensors at multiple depths. Visualization of the moisture profiles of soils of various textures and water management regimes enables us to study the dynamics of water transport in porous media such as soils.

The decision tools provided by the disclosed system 1000 are used for effective management of irrigation, and overall vineyard management (when and how much fruit to drop, pruning, canopy management, irrigation schedule), supply ordering for harvest and wine production, scheduling of harvest, etc.

In one embodiment, the system 1000 evaluates information received from sensors 1021 for multiple previous growing seasons or years, and uses the information to predict irrigation volume and timing patterns that will be optimal for the current growing season or year. The system 1000 may further be operatively connected to automatic irrigation systems and enable automatic control of the irrigation volume and timing based on the received information. The system 1000 may also utilize other information to determine the optimal irrigation volume and timing patterns may also be determined based on additional information, including enological research, historical weather and microclimate patterns, and soil structure information. The system 1000 may also evaluate the received data variation spatially and temporally, as it relates to the composition of the fruit (e.g., grapes) and an entire crop at harvest or different stages of plant growth.

In a further embodiment, the system 1000 evaluates the spatial density of the moisture information received from the sensors, applies a spatial density estimation technique which utilizes a multivariate adaptive kernel density estimation technique in combination with temporal predictive analytic technique and anomaly detection technique to further determine optimal irrigation volume and timing. The system 1000 may further utilize predictive weather models to determine the optimal irrigation volume and timing.

In further embodiments, the system 1000 utilizes the received information to predict optimal harvest dates and update those predictions as new microclimate, soil moisture, and weather data is updated—at a map block or subblock level. In addition, the system 1000 can be configured to predict the composition variation and amounts of key grape attributes down to the 3 m×3 m resolution as well as aggregate average value across map blocks and subblocks based on derived information from sensors 1021, models, soil, weather, and initial veraison grape analysis data. The data may also be used to create detailed spatial variation maps indicating key component areas that are on target, above target or below target with respect to plant growth and development.

Figure 2:
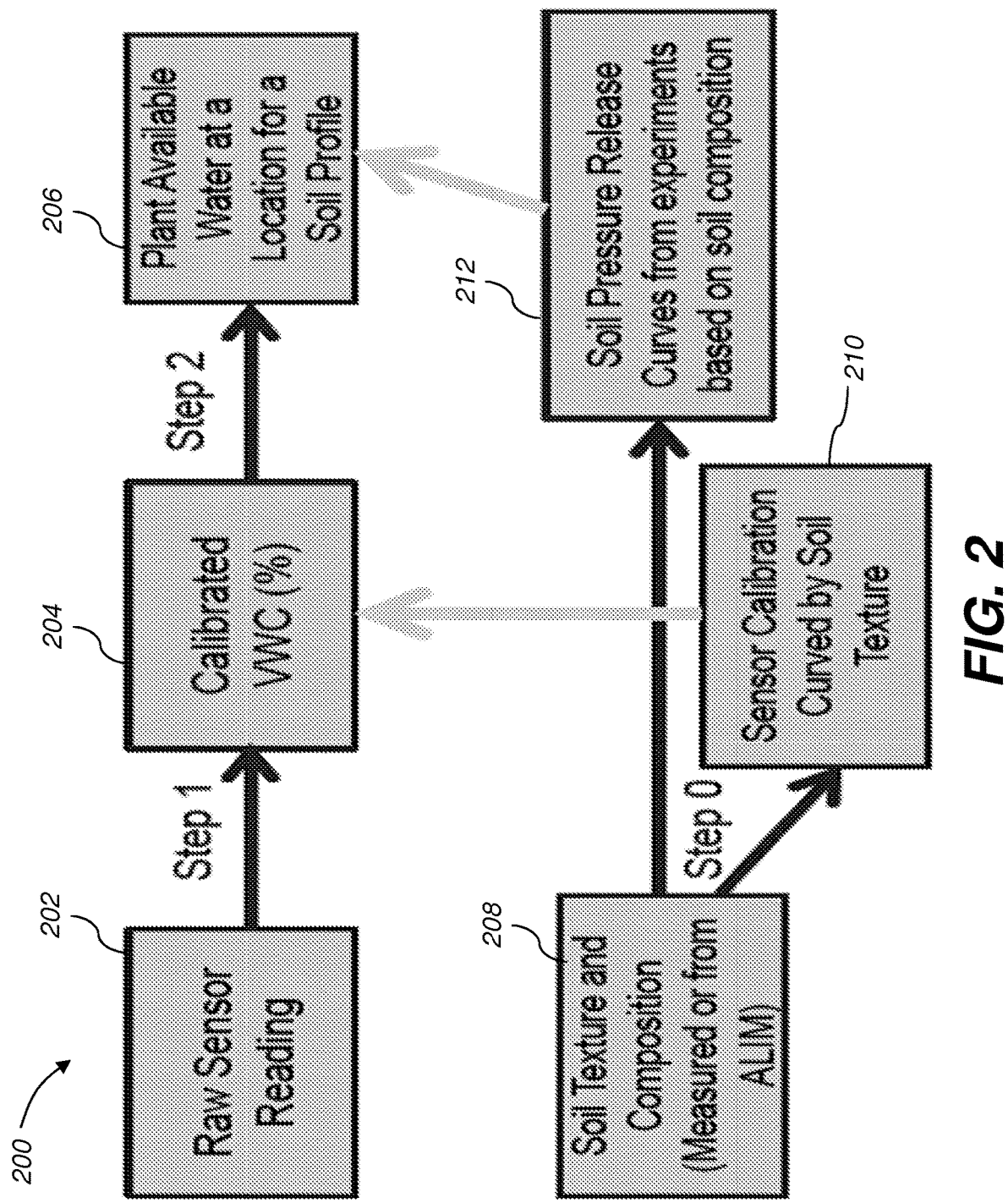
FIG. 2 shows a process for analyzing soil data according to one embodiment.

FIG. 2 is a process flow 200 for an embodiment of a logic model depicting the analysis of data received from the soil sensors (1021 in FIG. 3) using the system 1000. At step 202, the raw sensor data is received from the sensors 1021. The data is then analyzed to determine volume water content (VWC) of the soil (step 204). At step 206, the plat available water for a given location where the sensor is located is determined and a soil profile is produced.

As another part of the process 200, soil texture composition is determined from the received sensor data or from available automatic landform inference mapping (ALIM) data, or from a combination of both (step 208). At step 210, the sensor data is calibrated to determine a curve based on the soil texture. This is used in step 204 to calibrate the VWC of the soil. The data from step 208 may also be used to determine soil pressure release curves from experiments based on soil composition. The data from step 212 can then be used to further determine the plant available water at step 206.

Figure 3:
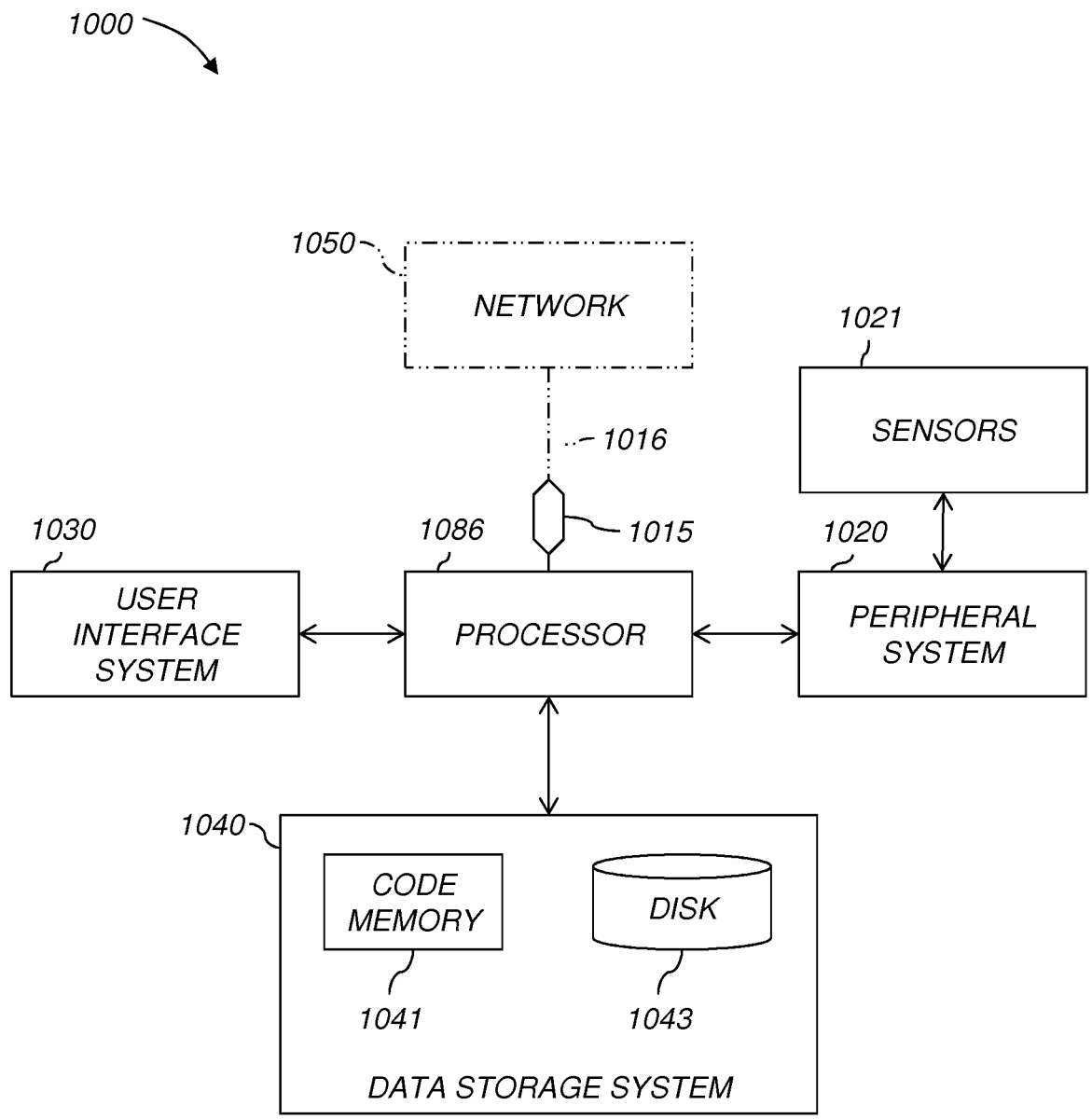
FIG. 3 is a high-level diagram showing the components of an exemplary crop management system for analyzing soil data and performing other analyses according to one embodiment.

FIG. 3 is a high-level diagram showing the components of the exemplary crop management system 1000 for analyzing soil data and performing other analyses described herein, and related components. The system 1000 includes a processor 1086, a peripheral system 1020, a user interface system 1030, and a data storage system 1040. The peripheral system 1020, the user interface system 1030 and the data storage system 1040 are communicatively connected to the processor 1086. Processor 1086 can be communicatively connected to network 1050 (shown in phantom), e.g., the Internet or a leased line, as discussed below. The moisture and temperature data may be received using sensors 1021 and/or displayed using display units (included in user interface system 1030) which can each include one or more of systems 1086, 1020, 1030, 1040, and can each connect to one or more network(s) 1050. Sensors 1021 may comprise temperature sensors, moisture sensors, pressure sensors, or any combination thereof. Processor 1086, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs).

Processor 1086 can implement processes of various aspects described herein. Processor 1086 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise. Processor 1086 can include Harvard-architecture components, modified-Harvard-architecture components, or Von-Neumann-architecture components.

The phrase "communicatively connected" includes any type of connection, wired or wireless, for communicating data between devices or processors. These devices or processors can be located in physical proximity or not. For example, subsystems such as peripheral system 1020, user interface system 1030, and data storage system 1040 are shown separately from the data processing system 1086 but can be stored completely or partially within the data processing system 1086.

The peripheral system 1020 can include one or more devices configured to provide digital content records to the processor 1086. For example, the peripheral system 1020 can include digital still cameras, digital video cameras, cellular phones, or other data processors. The processor 1086, upon receipt of digital content records from a device in the peripheral system 1020, can store such digital content records in the data storage system 1040.

The user interface system 1030 can include a mouse, a keyboard, another computer (connected, e.g., via a network or a null-modem cable), or any device or combination of devices from which data is input to the processor 1086. The user interface system 1030 also can include a display device, a processor-accessible memory, or any device or combination of devices to which data is output by the processor 1086. The user interface system 1030 and the data storage system 1040 can share a processor-accessible memory.

In various aspects, processor 1086 includes or is connected to communication interface 1015 that is coupled via network link 1016 (shown in phantom) to network 1050. For example, communication interface 1015 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WiFi or GSM. Communication interface 1015 sends and receives electrical, electromagnetic or optical signals that carry digital or analog data streams representing various types of information across network link 1016 to network 1050. Network link 1016 can be connected to network 1050 via a switch, gateway, hub, router, or other networking device.

Processor 1086 can send messages and receive data, including program code, through network 1050, network link 1016 and communication interface 1015. For example, a server can store requested code for an application program (e.g., a JAVA applet) on a tangible non-volatile computer-readable storage medium to which it is connected. The server can retrieve the code from the medium and transmit it through network 1050 to communication interface 1015.

The received code can be executed by processor 1086 as it is received, or stored in data storage system 1040 for later execution.

Data storage system 1040 can include or be communicatively connected with one or more processor-accessible memories configured to store information. The memories can be, e.g., within a chassis or as parts of a distributed system. The phrase "processor-accessible memory" is intended to include any data storage device to or from which processor 1086 can transfer data (using appropriate components of peripheral system 1020), whether volatile or non-volatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMs). One of the processor-accessible memories in the data storage system 1040 can be a tangible non-transitory computer-readable storage medium, i.e., a non-transitory device or article of manufacture that participates in storing instructions that can be provided to processor 1086 for execution.

In an example, data storage system 1040 includes code memory 1041, e.g., a RAM, and disk 1043, e.g., a tangible computer-readable rotational storage device such as a hard drive. Computer program instructions are read into code memory 1041 from disk 1043. Processor 1086 then executes one or more sequences of the computer program instructions loaded into code memory 1041, as a result performing process steps described herein. In this way, processor 1086 carries out a computer implemented process. For example, steps of methods described herein, blocks of the flowchart illustrations or block diagrams herein, and combinations of those, can be implemented by computer program instructions. Code memory 1041 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein may be embodied as computer program products including computer readable program code stored on a tangible non-transitory computer readable medium. Such a medium can be manufactured as is conventional for such articles, e.g., by pressing a CD-ROM. The program code includes computer program instructions that can be loaded into processor 1086 (and possibly also other processors), to cause functions, acts, or operational steps of various aspects herein to be performed by the processor 1086 (or other processor). Computer program code for carrying out operations for various aspects described herein may be written in any combination of one or more programming language(s), and can be loaded from disk 1043 into code memory 1041 for execution. The program code may execute, e.g., entirely on processor 1086, partly on processor 1086 and partly on a remote computer connected to network 1050, or entirely on the remote computer.

Those skilled in the art will recognize that numerous modifications can be made to the specific implementations described above. The implementations should not be limited to the particular limitations described. Other implementations may be possible.

The invention claimed is:

1. A method, comprising:
using a computer, receiving sensor data from a plurality of disposed within an agricultural field in at least two locations throughout a soil profile and at at least two depths within a crop root zone, at least one of which is equal to or more than 1 foot beneath a surface of the field, wherein the sensor data comprises one or more of temperature, electrical conductivity and moisture data;
generating a spatial map of the agricultural field based on at least topography data of the field;
determining a volumetric water content for at least one area of soil contained in the field using the sensor data and taking into account a level of spatial and temporal variability within the area and any vertical variability through a root zone of the area of soil;
calibrating the volumetric water content of each the area of soil using at least data relating to soil composition for at least one area;
reflecting the calibrated volumetric water content data and the data relating to soil composition in the spatial map;
determining a plant available water level for each area of soil; and
displaying results of said evaluating on an electronic interface to a user to provide a three-dimensional assessment of water movement through the soil and across the field.

2. The method according to claim 1, further comprising:
determining a soil texture and composition profile for each area of soil using the spatial map, data received from the sensors at at least two depths within the root zone of each area of soil, or both;
wherein the sensors are positioned in at least 1 foot vertical depth intervals when in the same area of soil.

3. The method according to claim 2, further comprising:
determining a sensor calibration curve based on the soil texture and composition profile; and
wherein the data relating to soil composition comprises automatic landform interference mapping (ALIM) data or ALIM data and sensor data.

4. The method according to claim 3, wherein calibrating the volumetric water content for each area of soil is further based on the sensor calibration curve.

5. The method according to claim 3,
wherein the sensor calibration curve is further determined from data received from the sensors.

6. The method according to claim 2, further comprising:
determining a soil pressure release curve based on the soil texture and composition profile for each area of the soil.

7. The method according to claim 6, further comprising:
adjusting the plant available water determination based on the soil pressure release curve.

8. The method according to claim 1, further comprising utilizing predictive weather models in conjunction with the volumetric water content, plant available water level of the soil level, and the water movement to determine irrigation volume and timing; and
wherein the spatial map comprises a resolution finer than 3 meters by 3 meters.

9. The method according to claim 1, further comprising:
for each of a plurality of soil areas, determining a weighted interpolation of plant available water in the soil area from plant available water levels determined for a plurality of points within the soil area.

10. The method according to claim 1, further comprising:
averaging determined values for plant available water; and
generating a flow simulation on an electronic display based on the averaged plant available water and the spatial map.

11. A system, comprising:
a memory;
a computer processor operatively connected to the memory;
and a plurality of sensors, each sensor configured to measure one or more of temperature, electrical conductivity, and moisture data, the plurality of sensors operatively connected to the processor and disposed within an agricultural field in at least two locations throughout a soil profile and at at least two depths within a crop root zone;
wherein the processor is configured to:
receive data from the plurality of sensors;
generate a spatial map of the agricultural field based on at least topography data of the field;
determine a volumetric water content for an area of soil contained in the field using the data received from the sensors, taking into account a level of spatial and temporal variability within the area and any variability through a root zone of the soil;
calibrate the volumetric water content of the area of soil using at least data relating to soil composition for the area of soil;
reflect the calibrated volumetric water content data in the spatial map;
determine a plant available water level for the area of soil; and
display results of said evaluating on an electronic interface to a user to provide a three-dimensional assessment of water movement through the soil and across the field.

12. The system of claim 11, the processor further configured to:
determine a soil texture and composition profile for the area of the soil using the spatial map, data received from the sensors, or both;
wherein at least one of the depths of the plurality of sensors is equal to or more than 1 foot beneath a surface of the field.

13. The system according to claim 12, the processor further configured to:
determine a sensor calibration curve based on the soil texture and composition profile.

14. The system according to claim 13, the processor further configured to:
calibrate the volumetric water content for the area of soil based on the sensor calibration curve.

15. The system according to claim 13, wherein the sensor calibration curve is further determined from data received from the sensors.

16. The system according to claim 13, wherein:
the processor is further configured to calibrate the volumetric water content of the area of soil using at least automatic landform interference mapping (ALIM) data relating to soil composition for the area of soil or at least the ALIM data and data from the plurality of sensors; and
the sensor calibration curve is further determined from the ALIM data.

17. The system according to claim 12, the processor further configured to:
determine a soil pressure release curve based on the soil texture and composition profile for the area of soil.

18. The system according to claim 17, the processor further configured to:
adjust the plant available water determination based on the soil pressure release curve.

19. The system according to claim 11, the processor further configured to:
for each of a plurality of soil areas, determine a weighted interpolation of plant available water in the soil area from plant available water levels determined for a plurality of points within the soil area.

20. The system according to claim 11, the processor further configured to:
average determined values for plant available water; and
using at least the spatial map, generate a flow simulation on an electronic display.

* * * * *